(12) United States Patent
Liu et al.

(10) Patent No.: US 12,385,076 B2
(45) Date of Patent: Aug. 12, 2025

(54) PREPARATION AND APPLICATION OF HIGH-ACTIVITY AND HIGH-SAFETY CARDAMINE VIOLIFOLIA SELENOPROTEIN STANDARD SAMPLE

(71) Applicant: ENSHI SE-RUN MATERIAL ENGINEERING TECHNOLOGY CO., LTD., Hubei (CN)

(72) Inventors: Haiyuan Liu, Hubei (CN); Xin Cong, Hubei (CN); Bo Xu, Hubei (CN); Yue Zhang, Hubei (CN); Jie Li, Hubei (CN); Cui Li, Hubei (CN); Zhenzhou Zhu, Hubei (CN); Shuiyuan Cheng, Hubei (CN)

(73) Assignee: ENSHI SE-RUN MATERIAL ENGINEERING TECHNOLOGY CO., LTD., Enshi (CN)

( * ) Notice: Subject to any disclaimer, the term of this patent is extended or adjusted under 35 U.S.C. 154(b) by 0 days.

(21) Appl. No.: 19/005,540

(22) Filed: Dec. 30, 2024

(65) Prior Publication Data
US 2025/0129402 A1    Apr. 24, 2025

Related U.S. Application Data

(63) Continuation of application No. PCT/CN2023/114545, filed on Aug. 23, 2023.

(30) Foreign Application Priority Data

Sep. 14, 2022    (CN) .......................... 202211119536.6

(51) Int. Cl.
| | | |
|---|---|---|
| A23J 1/00 | (2006.01) | |
| A23J 3/34 | (2006.01) | |
| C07K 1/36 | (2006.01) | |
| C12N 9/42 | (2006.01) | |
| C12N 9/76 | (2006.01) | |
| C12P 21/06 | (2006.01) | |

(52) U.S. Cl.
CPC ................ *C12P 21/06* (2013.01); *C07K 1/36* (2013.01); *C12N 9/2437* (2013.01); *C12N 9/6427* (2013.01); *C12Y 302/01004* (2013.01); *C12Y 304/21004* (2013.01); *C12Y 304/21062* (2013.01); *C12Y 304/21064* (2013.01); *C12Y 304/22002* (2013.01)

(58) Field of Classification Search
CPC .. A23J 1/00; A23J 3/34; C12N 9/2437; C12N 9/6427; C07K 1/36
See application file for complete search history.

(56) References Cited

U.S. PATENT DOCUMENTS

4,486,282 A    12/1984  Bier

FOREIGN PATENT DOCUMENTS

| CN | 104744110 A | 7/2015 |
|----|-------------|--------|
| CN | 105795095 A | 7/2016 |
| CN | 106916871 A | 7/2017 |
| CN | 107815483 A | 3/2018 |
| CN | 108157579   | * 6/2018 |
| CN | 110256600 A | 9/2019 |
| CN | 111748046 A | 10/2020 |
| CN | 112515032 A | 3/2021 |
| CN | 112535233 A | 3/2021 |

OTHER PUBLICATIONS

Shocron et al., Environ. Sci. Technol. Lett., 2022, 9, 889-899.*
Notification to Grant Patent Right for Invention, Japanese Patent Application No. 2024-509147, mailed Nov. 19, 2024 (3 pages).
Zhu Song et al., "Antioxidant and anti-fatigue activities of selenium-enriched peptides isolated from Cardamine violifolia protein hydrolysate", Journal of Functional Foods, 79, 104412, date of issue 2021.
Zhu Song et al., "Antioxidant Activity of Selenium-Enriched Peptides from the Protein Hydrolysate of Cardamine violifolia", Journal of Food Science, vol. 84, Issue 12, pp. 3504-3511, date of issue 2019.

* cited by examiner

*Primary Examiner* — Maryam Monshipouri
(74) *Attorney, Agent, or Firm* — HOWARD M COHN and Associates, LLC

(57) ABSTRACT

The present disclosure provides a preparation and application of high-activity and high-safety *Cardamine violifolia* selenoprotein standard sample. The standard sample of the *Cardamine violifolia* selenoprotein prepared by the present disclosure has the advantages of extremely low heavy metal content, less ash, high protein content, high total selenium content, high organic selenium ratio of up to 99.9%, high biological activity, high safety and so on; the organic selenium is mainly in form of selenocysteine/selenocystine and accounts for more than 90% of the total selenium content, and is expected to make up for the shortage of selenoprotein standard samples on the market.

7 Claims, 3 Drawing Sheets

PREPARATION AND APPLICATION OF HIGH-ACTIVITY AND HIGH-SAFETY CARDAMINE VIOLIFOLIA SELENOPROTEIN STANDARD SAMPLE

CROSS REFERENCE OF RELATED APPLICATIONS

The present application is a continuation-application of International Patent Application (PCT) No. PCT/CN2023/114545 filed on Aug. 23, 2023, which claims foreign priority of Chinese Patent Application No. 202211119536.6, filed on Sep. 14, 2022, the entire contents of which are hereby incorporated by reference.

TECHNICAL FIELD

The present disclosure relates to the technical field of selenoprotein, specifically to a preparation process of a high-activity and high-safety *Cardamine violifolia* selenoprotein standard sample and the application of the obtained *Cardamine violifolia* selenoprotein standard sample in the preparation of food and pharmaceuticals.

BACKGROUND

"GB1903.28-2018 Food Safety National Standard, Food Nutrition Fortifier Selenium Protein" discloses a selenoprotein standard. This standard stipulates that the source of selenoprotein is edible plants such as soybeans with high selenium content, which are refined into a food nutrition fortifier rich in selenomethionine through defatting, water extraction, ethanol precipitation, and drying. However, due to the generally low selenium content of soybean raw materials and insufficient refining technology, there has been no relevant selenoprotein products that meet the standards on the market, and even laboratory standard samples are difficult to prepare, which poses a huge obstacle to industrial application. In addition, according to research, selenocysteine/selenocystine is safer than selenomethionine, and selenocysteine has been defined by the academic community as the 21st essential amino acid for the human body. Therefore, selenoproteins with high biological activity, high safety, and high selenocysteine/selenocystine content have important application value.

Plants with high selenium content, such as broccoli, cabbage, *Cardamine violifolia*, rice, etc., usually also contain more heavy metal pollutants, these heavy metals are mainly cadmium, lead, arsenic, etc. The reason is that the heavy metal content in the selenium-rich soil where selenium-rich plants are planted is usually relatively high, and selenium and cadmium coexist; so the plants will also be enriched with a certain amount of heavy metals while being selenium-rich, resulting in excessive heavy metals in the plants, which in turn poses a food safety hazard. Among them, *Cardamine violifolia* (*Cardamine violifolia* O. E. Schulz) is a plant with a super strong ability to accumulate selenium, and its organic selenium form is mainly selenocysteine (calculated as selenocystine). However, at present, *Cardamine violifolia* is mostly eaten directly, or used as a food raw material after drying and crushing, or directly used as a food raw material after simple extraction or extraction with organic solvents. Therefore, when the background value of heavy metals in the soil is high, there is a greater risk of heavy metal contamination of food. At the same time, since heavy metals mostly form complexes with proteins or peptides, they are present in plants as a component of the active center of enzymes, such as plant chelating peptides, which improve the tolerance of plants to heavy metals; aqueous extraction and simple organic solvent extraction cannot effectively destroy the combination between heavy metals and chelating peptides and cannot achieve effective removal of heavy metals.

At present, most of the extraction of plant organic selenoproteins uses organic solvents, strong acids and alkalis, ethanol, etc., which not only easily destroy the quaternary structure of selenoproteins, resulting in reduced stability of functional components and inactivation to varying degrees, but also produce a lot of wastewater and waste liquid, causing serious environmental pollution and hidden dangers in production safety. The conventional aqueous extraction method has high heavy metal content and ash content, which poses a hidden danger to food safety; at the same time, the selenium form of the separated components is unclear, and its efficacy, activity and safety are not guaranteed.

SUMMARY

In view of the problems in the prior art, the present disclosure provides a preparation process for producing a selenoprotein standard sample with low heavy metal content, high bioactivity, high safety and high selenocysteine/selenocystine content by taking *Cardamine violifolia* as a raw material. The selenocysteine/selenocystine content in the selenoprotein standard sample prepared by the preparation process can occupy more than 90% of the total selenium content, and indexes such as the total selenium content, the heavy metal content, the protein content and the characteristic organic selenium form are all achieved and significantly better than those of the selenoprotein national standard.

The technical solution of the present disclosure is shown as follows:

The preparation method of standard sample of selenoprotein in *Cardamine violifolia*, the preparation method is high-activity and high-safety, the preparation method comprises following steps:

step 1, hydrolyzing *Cardamine violifolia* powder with cellulase, performing cellulase deactivation treatment after the hydrolyzing, and then centrifuging to obtain a supernatant;

step 2, adding compound enzymes into the supernatant for continuous enzymolysis treatment, and synchronously performing electrodialysis to dissociate compounded heavy metal ions; removing inorganic selenium salt ions and the heavy metal ions by the electrodialysis and then performing compound enzymes deactivation treatment, a reaction solution is obtained; wherein the compound enzymes are composed of alkaline protease, trypsin, papain, protease K and protease XIV;

step 3, concentrating and drying the reaction solution obtained in step 2 to obtain the standard sample of selenoprotein in *Cardamine violifolia*.

Specifically, in some embodiments, the cellulase, used in step 1, is an amount of 0.1~10 wt % of the *Cardamine violifolia* powder; a temperature of the hydrolyzing is 30~50° C., and a time of the hydrolyzing is 1~4 h.

In some embodiments, the centrifugal parameter, in step 1, is 1000~10000 r/min for 5~60 min; performing centrifugation to remove some large insoluble particles that remain after cellulase hydrolysis.

In some embodiments, the compound enzymes, in step 2, is an amount of 0.1~10 wt % of the *Cardamine violifolia* powder; a temperature of the continuous enzymolysis treatment is 30~50° C.; further, the mass ratio of alkaline protease, trypsin, papain, protease K and protease XIV in the compound enzymes is 1:1:1:1:1.

In some embodiments, the electrodialysis parameter in step 2 is as follows: a voltage of 15~100 V, a current of 10 Å or less, a flow rate of a polar water is 1~100 L/h, a flow rate of a fresh water is 1~100 L/h, a flow rate of a concentrated water is 1~100 L/h, a volume ratio of the fresh water and the concentrated water is 1:1, wherein the polar water is 0.1~10 wt % sodium sulfate solution.

In some embodiments, the time of the continuous enzymolysis treatment is 0.5~8 h and the time of the electrodialysis is 0.5~8 h.

In some embodiments, the temperature of the cellulase deactivation treatment and the compound enzymes deactivation treatment were both 85~95° C.

In some embodiments, the drying, in step 3, is spray drying or freeze drying. The beneficial effects of the present disclosure are:

1) Firstly, decomposing the fiber bound to the protein in *Cardamine violifolia* with a cellulose enzyme to release an organic selenium-rich protein; then, the enzyme-digested macromolecular protein is directionally digested by the compound enzymes as an amino acid; moreover, the compound enzymes provided by the present disclosure can efficiently and selectively dissociate selenocysteine/selenocystine to the greatest extent; the compound enzymes can dissociate the heavy metal compounded with the protein to form free heavy metal ions while performing enzymolysis; removing the heavy metal ions and the inorganic selenium in cooperation with an electrodialysis technology, without affecting the stability of the selenoprotein characterized by the high-activity selenocysteine/selenocystine;

2) In the present disclosure, the enzymolysis conditions are mild and the enzymolysis time is short, and strong acid and strong bases and organic solvents are not used, so that steady-state conversion and physiological activity retention of the organic selenium form of selenocysteine/selenocystine can be obtained and protected to the greatest extent;

3) The present disclosure finds that electrodialysis can promote efficient and selective dissociation of selenoproteins rich in selenocysteine/selenocystine;

4) In the *Cardamine violifolia* selenoprotein standard sample prepared by the present disclosure, the selenium form is mainly selenocysteine/selenocystine and its content can reach more than 90% of the total selenium content. The safety of selenocysteine/selenocystine is higher than that of selenomethionine. The present disclosure also further verifies its high activity and high safety through animal experiments and applications;

5) The total selenium content in the *Cardamine violifolia* selenoprotein standard sample prepared by the present disclosure is 1500-5000 mg/kg, and the proportion of organic selenium content in the total selenium content can reach 99.9% or more, which is much higher than the organic selenium content required in "DBS42/002-2022 Requirements for Selenium Content in Organic Selenium-Rich Foods", which is more than 80%. Therefore, the safety risks caused by inorganic selenium residues can be almost eliminated, so it is safer; the protein content in the selenoprotein is greater than or equal to 60%; heavy metals such as lead, arsenic, mercury, and cadmium in the extract are not detected, and the ash content is reduced to 2% or less, so it is also safer. In summary, the various parameters of the *Cardamine violifolia* selenoprotein standard sample obtained by the present disclosure can meet or significantly exceed the requirements of the national standard for selenoproteins, as shown in the following table:

| Technical indicators | *Cardamine violifolia* selenoprotein prepared by the present disclosure | Selenoprotein national standard |
| --- | --- | --- |
| Selenium content /mg/kg | 1500-5000 | 1000-2500 |
| Organic selenium forms and their mass percentage in total selenium w/% | Selenocysteine/Selenocystine ≥90% | Selenomethionine ≥80% |
| Protein Content w/% | ≥60% | ≥40% |
| Ash Content /% | ≤2% | ≤10% |
| (As) /mg/kg | Not detected | ≤0.5 |
| (Pb) /mg/kg | Not detected | ≤1 |
| (Hg) /mg/kg | Not detected | ≤0.1 |
| (Cd) /mg/kg | Not detected | ≤1 |

The *Cardamine violifolia* selenoprotein standard sample prepared by the present disclosure is expected to make up for the shortage of selenoprotein standard samples on the market.

DETAILED DESCRIPTION

Figure 1:
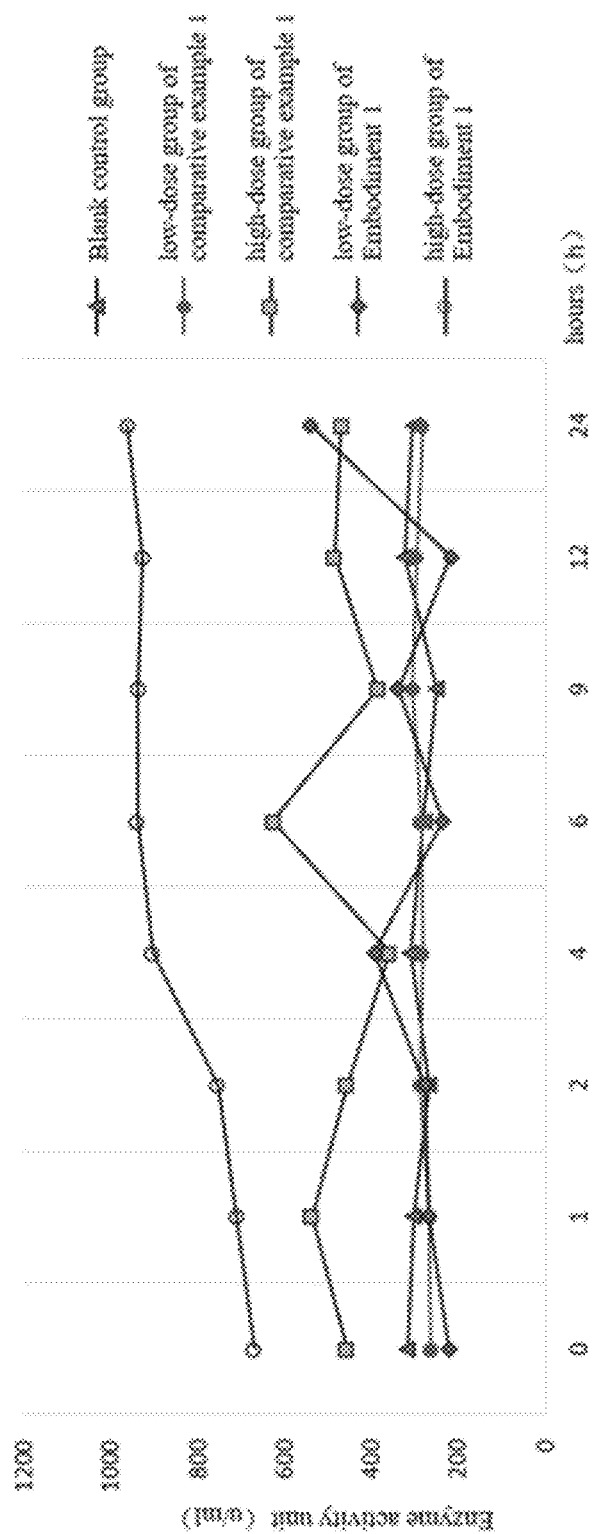
FIG. 1 is a graph of enzyme activity variation of serum glutathione peroxidase for a single administration of a selenium formulation.

The present disclosure is described in detail in combination with the embodiments and attached drawings. The following embodiments are implemented on the premise of the technical scheme of the present disclosure, and the detailed implementations and specific operation processes are given. However, the scope of protection of the present disclosure is not limited to the following embodiments.

In the following embodiments, unless otherwise specified, all methods are conventional methods; the reagents and materials described, unless otherwise specified, can be obtained from commercial sources.

Embodiment 1

The preparation process of the *Cardamine violifolia* selenoprotein in present embodiment is specifically as follows:
  (1) drying and then crushing the crushed *Cardamine violifolia* through a 40-mesh sieve; adding *Cardamine violifolia* powder and cellulase (the mass ratio of the two is 1:0.02) to pure water and undergoing oscillation enzymolysis at 40° C. for 2 h; then raising temperature to 85° C. for enzyme deactivation treatment; then centrifuging at 3000 r/min for 15 min to remove precipitated impurities; and collecting supernatant.
  (2) Adding compound enzymes composed of alkaline protease, trypsin, papain, protease K and protease XIV (1:1:1:1:1) to the supernatant; the mass ratio of the addition amount of the compound enzymes to the *Cardamine violifolia* powder is 0.015:1; placing the supernatant added with the compound enzymes in an electrodialyzer for synchronous electrodialysis and the working parameters of the electrodialyzer are as follows: voltage 15V, current 3.3 A, polar water flow rate 12 L/h, fresh water and concentrated water flow rate 20 L/h, fresh water and concentrated water volume ratio of 1:1, and the polar water is 2% sodium sulfate solution. In the present process, the temperature of the enzymatic hydrolysis reaction solution is kept at 45° C. for 2 h; heating the reaction solution to 85° C. for enzyme deactivation treatment after completing reaction, and collecting filtrate.

(3) Concentrating the filtrate in vacuo and then spray-drying to obtain the target product.

Embodiment 2

The preparation process of the *Cardamine violifolia* selenoprotein in present embodiment is specifically as follows:
(1) drying and then crushing the crushed *Cardamine violifolia* through a 40-mesh sieve; adding the *Cardamine violifolia* powder and cellulase (the mass ratio of the two is 1:0.02) to pure water and undergoing oscillation enzymolysis at 40° C. for 2 h; then raising temperature to 85° C. for enzyme deactivation treatment; then centrifuging at 3000 r/min for 15 min to remove precipitated impurities; and collecting supernatant.
(2) Adding a compound enzyme composed of alkaline protease, trypsin, papain, protease K and protease XIV (1:1:1:1:1) to the supernatant; the mass ratio of the addition amount of the compound enzyme to the *Cardamine violifolia* powder is 0.015:1; placing the supernatant added with the compound enzyme in an electrodialyzer for synchronous electrodialysis and the working parameters of the electrodialyzer are as follows: voltage 13V, current 3 A, polar water flow rate 15 L/h, fresh water and concentrated water flow rate 22 L/h, fresh water and concentrated water volume ratio of 1:1, and the polar water is 2% sodium sulfate solution. In present process, the temperature of the enzymatic hydrolysis reaction solution is kept at 45° C. for 2 h; heating the reaction solution to 85° C. for enzyme deactivation treatment after completing reaction, and collecting filtrate.
(3) Concentrating the filtrate in vacuo and then spray-drying to obtain the target product.

COMPARATIVE EXAMPLE 1

The preparation process of the *Cardamine violifolia* selenoprotein in present Comparative Example is specifically as follows:
(1) drying and then crushing the crushed *Cardamine violifolia* through a 40-mesh sieve; adding the *Cardamine violifolia* powder and cellulase (the mass ratio of the two is 1:0.02) to pure water and undergoing oscillation enzymolysis at 40° C. for 2 h; then raising temperature to 85° C. for enzyme deactivation treatment; then centrifuging at 3000 r/min for 15 min to remove precipitated impurities; and collecting supernatant.
(2) Adding a compound enzyme composed of alkaline protease, trypsin, papain, protease K and protease XIV (1:1:1:1:1) to the supernatant; the mass ratio of the addition amount of the compound enzyme to the *Cardamine violifolia* powder is 0.015:1; the temperature of the enzymatic hydrolysis reaction solution is kept at 45° C. for 2 h; heating the reaction solution to 85° C. for enzyme deactivation treatment after completing reaction, and collecting filtrate.
(3) Concentrating the filtrate in vacuo and then spray-drying to obtain the target product.

COMPARATIVE EXAMPLE 2

The preparation process of the *Cardamine violifolia* selenoprotein in present Comparative Example is specifically as follows:
(1) drying and then crushing the crushed *Cardamine violifolia* through a 40-mesh sieve; adding the *Cardamine violifolia* powder and cellulase (the mass ratio of the two is 1:0.02) to pure water and undergoing oscillation enzymolysis at 40° C. for 2 h; then raising temperature to 85° C. for enzyme deactivation treatment; then centrifuging at 3000 r/min for 15 min to remove precipitated impurities; and collecting supernatant.
(2) placing the supernatant in an electrodialyzer for synchronous electrodialysis and the working parameters of the electrodialyzer are as follows: voltage 15V, current 3.3 A, polar water flow rate 12 L/h, fresh water and concentrated water flow rate 20 L/h, fresh water and concentrated water volume ratio of 1:1, and the polar water is 2% sodium sulfate solution. In the present process, the temperature of the enzymatic hydrolysis reaction solution is kept at 45° C. for 2 h; collecting filtrate after completing reaction.
(3) Concentrating the filtrate in vacuo and then spray-drying to obtain the target product.

COMPARATIVE EXAMPLE 3

The preparation process of the *Cardamine violifolia* selenoprotein in present Comparative Example is specifically as follows:
(1) drying and then crushing the crushed *Cardamine violifolia* through a 40-mesh sieve; adding the *Cardamine violifolia* powder to pure water and undergoing oscillation extraction at 40° C. for 2 h; then centrifuging at 3000 r/min for 15 min to remove precipitated impurities; and collecting supernatant.
(2) placing the supernatant in an electrodialyzer for synchronous electrodialysis and the working parameters of the electrodialyzer are as follows: voltage 15V, current 3.3 A, polar water flow rate 12 L/h, fresh water and concentrated water flow rate 20 L/h, fresh water and concentrated water volume ratio of 1:1, and the polar water is 2% sodium sulfate solution. In the present process, the temperature of the enzymatic hydrolysis reaction solution is kept at 45° C. for 2 h; collecting filtrate after completing reaction.
(3) Concentrating the filtrate in vacuo and then spray-drying to obtain the target product.

COMPARATIVE EXAMPLE 4

The preparation process of the *Cardamine violifolia* selenoprotein in present Comparative Example is specifically as follows:
(1) drying and then crushing the crushed *Cardamine violifolia* through a 40-mesh sieve; adding the *Cardamine violifolia* powder and cellulase (the mass ratio of the two is 1:0.02) to pure water and undergoing oscillation enzymolysis at 40° C. for 2 h; then raising temperature to 85° C. for enzyme deactivation treatment; then centrifuging at 3000 r/min for 15 min to remove precipitated impurities; and collecting supernatant.
(2) Adding a compound enzyme composed of alkaline protease, trypsin, papain, protease K and protease XIV (1:1:1:1:1) to the supernatant; the mass ratio of the addition amount of the compound enzyme to the *Cardamine violifolia* powder is 0.015:1; the temperature of the enzymatic hydrolysis reaction solution is kept at 45° C. for 2 h; heating the reaction solution to 85° C. for enzyme deactivation treatment after completing reaction, and collecting filtrate.
(3) treating the filtrate collected in previous step for synchronous electrodialysis and the working parameters of the electrodialyzer are as follows: voltage 15V, current 3.3 A, polar water flow rate 12 L/h, fresh water and concentrated water flow rate 20 L/h, fresh water and concentrated water volume ratio of 1:1, and the polar water is 2% sodium sulfate solution. In the present process, the temperature of the enzymatic hydrolysis reaction solution is kept at 45° C. for 2 h; collecting filtrate after completing reaction.
(4) Concentrating the filtrate in vacuo and then spray-drying to obtain the target product.

COMPARATIVE EXAMPLE 5

The preparation process of the *Cardamine violifolia* selenoprotein in present Comparative Example is specifically as follows:
(1) drying and then crushing the crushed *Cardamine violifolia* through a 40-mesh sieve; adding the *Cardamine violifolia* powder and cellulase (the mass ratio of the two is 1:0.02) to pure water and undergoing oscillation enzymolysis at 40° C. for 2 h; then raising temperature to 85° C. for enzyme deactivation treatment; then centrifuging at 3000 r/min for 15 min to remove precipitated impurities; and collecting supernatant.
(2) Adding a compound enzyme composed of alkaline protease, trypsin, proteinase E, neutral protease and protease K (1:1:1:1:1) to the supernatant; the mass ratio of the addition amount of the compound enzyme to the *Cardamine violifolia* powder is 0.015:1; placing the supernatant added with the compound enzyme in an electrodialyzer for synchronous electrodialysis and the working parameters of the electrodialyzer are as follows: voltage 15V, current 3.3 A, polar water flow rate 12 L/h, fresh water and concentrated water flow rate 20 L/h, fresh water and concentrated water volume ratio of 1:1, and the polar water is 2% sodium sulfate solution. In present process, the temperature of the enzymatic hydrolysis reaction solution is kept at 45° C. for 2 h; heating the reaction solution to 85° C. for enzyme deactivation treatment after completing reaction, and collecting filtrate.
(3) Concentrating the filtrate in vacuo and then spray-drying to obtain the target product.

The following detections were performed on the *Cardamine violifolia* selenoprotein prepared in Embodiments 1~2 and Comparative Examples 1~5, specifically including two parts:

(1) Component Analysis

The protein content in each selenoprotein sample was detected by the method of GB 5009.5, the ash content was detected by the method of GB 5009.4, the total selenium content was detected by the method of GB 5009.93, the organic selenium content was detected by the method of DSB42/002, the proportion of selenocysteine (calculated as selenocystine, because free selenocysteine is extremely unstable, two molecules of selenocysteine will combine into one molecule of selenocystine) was detected by the method of T/CHC1001, the lead content was detected by the method of GB 5009.75, the arsenic content was detected by the method of GB 5009.76, the cadmium content was detected by the method of GB 5009.12, and the mercury content was detected by the method of GB 5009.17. The results are shown in the following table:

|  | Total selenium content mg/kg | The mass ratio of organic selenium to total selenium (%) | Selenocystine mass ratio to total selenium (%) | Lead content mg/kg |
|---|---|---|---|---|
| Embodiment 1 | 3330 | 99.95 | 91.25 | Not detected |
| Embodiment 2 | 3230 | 99.92 | 93.61 | Not detected |
| Comparative Example 1 | 2217 | 93.88 | 28.35 | 0.12 |
| Comparative Example 2 | 1609 | 88.52 | 28.11 | 0.1 |
| Comparative Example 3 | 1485 | 92.15 | 27.92 | 0.11 |
| Comparative Example 4 | 2380 | 90.95 | 55.63 | Not detected |
| Comparative Example 5 | 2416 | 90.28 | 53.70 | 0.04 |

|  | Arsenic content mg/kg | Cadmium content mg/kg | Total Mercury (Hg)/mg/kg | Protein Content (%) | Ash content (%) |
|---|---|---|---|---|---|
| Embodiment 1 | Not detected | Not detected | Not detected | 62.8 | 1.8 |
| Embodiment 2 | Not detected | Not detected | Not detected | 63.2 | 1.7 |
| Comparative Example 1 | 0.54 | 3.55 | 0.12 | 25.6 | 32.8 |
| Comparative Example 2 | 0.41 | 2.75 | 0.15 | 19.5 | 31.6 |
| Comparative Example 3 | 0.47 | 2.72 | 0.13 | 18.1 | 33.9 |
| Comparative Example 4 | Not detected | Not detected | Not detected | 50.6 | 2.1 |
| Comparative Example 5 | 0.11 | 0.36 | 0.03 | 49.8 | 2.3 |

From the data of the embodiments and comparative examples, it can be seen that electrodialysis can effectively reduce the contents of various heavy metals, inorganic selenium and ash, thereby increasing the protein content in the sample; and synchronous composite enzymatic hydrolysis and electrodialysis treatment can significantly increase the content of selenocystine; the reason being that: firstly, due to the use of an enzymatic hydrolysis combination to more fully hydrolyze the components of *Cardamine violifolia*, the heavy metals compounded with proteins can be fully dissociated; during the enzymatic hydrolysis process, the precipitation of metal ions occurs gradually, so that electrodialysis has enough time to fully remove the heavy metal components, and the dissociated heavy metal components are quickly removed by the simultaneous process of enzymatic hydrolysis and electrodialysis; thereby reducing the structural changes of biologically active components such as selenocystine in a heavy metal environment, and retaining the stability and biological activity of selenocystine to the greatest extent; secondly, the enzymatic hydrolysis combination provided by the present application can also more fully expose or separate the *Cardamine violifolia* protein from the *Cardamine violifolia* plant tissue, and at the same time, the *Cardamine violifolia* protein can be more fully enzymatically hydrolyzed into various peptides or amino acid fragments through the enzymatic hydrolysis combination, so that selenocystine can be dissociated to the greatest extent and maintain the most stable state in this enzymatic hydrolysis system; in addition, since the active center of human selenoprotein is selenocysteine, maintaining the activity of selenoprotein/selenoenzyme with selenocysteine as the active center is crucial to the regulation of human antioxidant balance, but the presence of heavy metals often changes the quaternary structure of proteases, resulting in reduced protein activity. Therefore, the method provided by the present application can further reduce the influence of heavy metals on the activity of selenoproteins characterized by selenocysteine/selenocystine, and further enhance their physiological activity on the basis of ensuring safety.

The selenoprotein standard sample prepared by the present disclosure has a total selenium content of up to 1500-5000 mg/kg, an organic selenium content of more than 99%, a selenocystine content of more than 90%, a protein content of more than 60%, an ash content that can be controlled below 2%, and no heavy metals such as lead, arsenic, mercury, and cadmium are detected. The above indicators (except that the organic selenium is in the form of selenocystine) fully meet the requirements of "GB1903.28-2018 National Food Safety Standard Food Nutrition Fortifier Selenium Protein".

(2) Antioxidant Activity Animal Experiment

To verify the enzyme activity of the standard sample of the *Cardamine violifolia* selenoprotein prepared by the present disclosure, the *Cardamine violifolia* selenoprotein prepared by Embodiment 1 and Comparative Example 1 were selected to perform the animal oxidation resistance Experiment, and the solution is shown as follows:

The experiment set up 4 test sample dosage groups and 1 control group. The 4 dosage groups were respectively the low-dose group of comparative example 1, the high-dose group of comparative example 1, the low-dose group of Embodiment 1, and the high-dose group of Embodiment 1. The dosages (in terms of selenium) were 0.03 mgSe/kg, 0.3 mgSe/kg, 0.02 mgSe/kg, and 0.2 mgSe/kg, respectively.

The test substance was prepared into a solution and mixed with feed for oral administration, and each animal completed oral intake within 1 minute. The control group was given an equal volume of distilled water. The number of animals in each test group was 4, and the control group was 2. The test substance was administered in two dosing cycles, with seven consecutive days as one dosing cycle, and the dosing frequency was once a day. A washout period was set between the two dosing cycles, the washout period of the comparative example 1 group was eight days, and the washout period of the Embodiment 1 group was ten days.

To observe the drug exposure level in animals, approximately 5 mL of whole blood was collected by anterior vena cava blood sampling and added to labeled blood collection tubes with K2EDTA as anticoagulant. The test index was the activity of serum glutathione peroxidase (GPX) after single and multiple administration of selenium preparations (preparing liver homogenate according to the kit instructions and testing with Nanjing Jiancheng Biological Kit).

Figure 2:
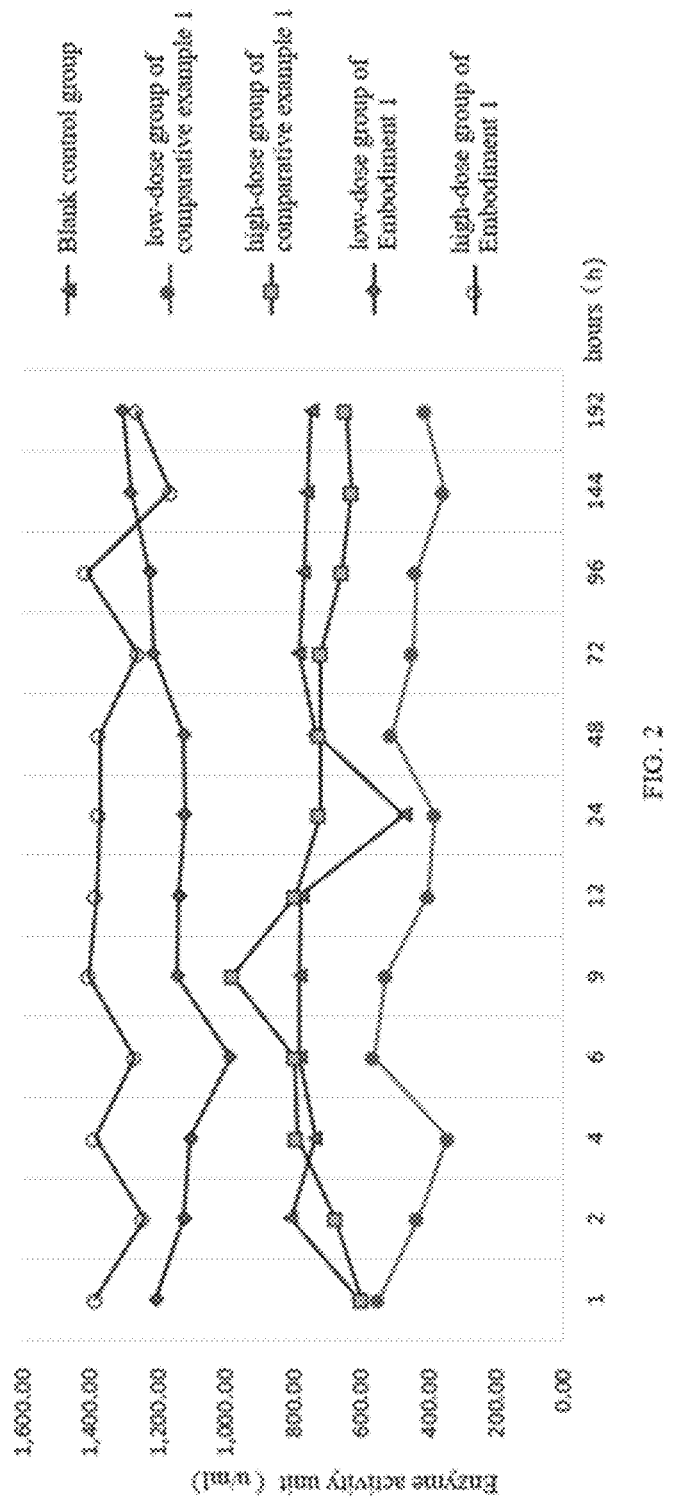
FIG. 2 is a graph of enzyme activity variation of serum glutathione peroxidase for multiple administration of a selenium formulation.

The test results are shown in FIG. 1 and FIG. 2, specifically: single or multiple administration of the *Cardamine violifolia* selenoprotein prepared in Comparative Example 1 has no significant effect on plasma GPX activity, a single administration of 0.14 mgSe/kg of the *Cardamine violifolia* selenoprotein prepared in Embodiment 1 can significantly increase plasma GPX activity, and multiple administrations of 0.03 mgSe/kg and 0.14 mgSe/kg of the *Cardamine violifolia* selenoprotein prepared in Embodiment 1 can significantly increase plasma GPX activity. Therefore, the *Cardamine violifolia* selenoprotein prepared in Embodiment 1 can significantly increase plasma GPX activity; the *Cardamine violifolia* selenoprotein prepared in Comparative Example 1 has no significant effect on plasma GPX activity.

(3) Safety Animal Testing

In this experiment, male rats were repeatedly given oral medication for 3 months to observe and explore the potential toxicity of the *Cardamine violifolia* selenoprotein prepared by the present disclosure (specifically prepared in Embodiment 1), sodium selenite, selenium-enriched yeast, and the selenoprotein sample prepared in Comparative Example 3 (the daily safety limit of selenium for adults is 400 μg/person; the safe dose in this experiment is equivalent to 96 μgSe/kg BW for the human body, which is equivalent to 5760 μg/day for an adult weighing 60 kg, which is nearly 15 times the daily safety limit for adults).

Figure 3:
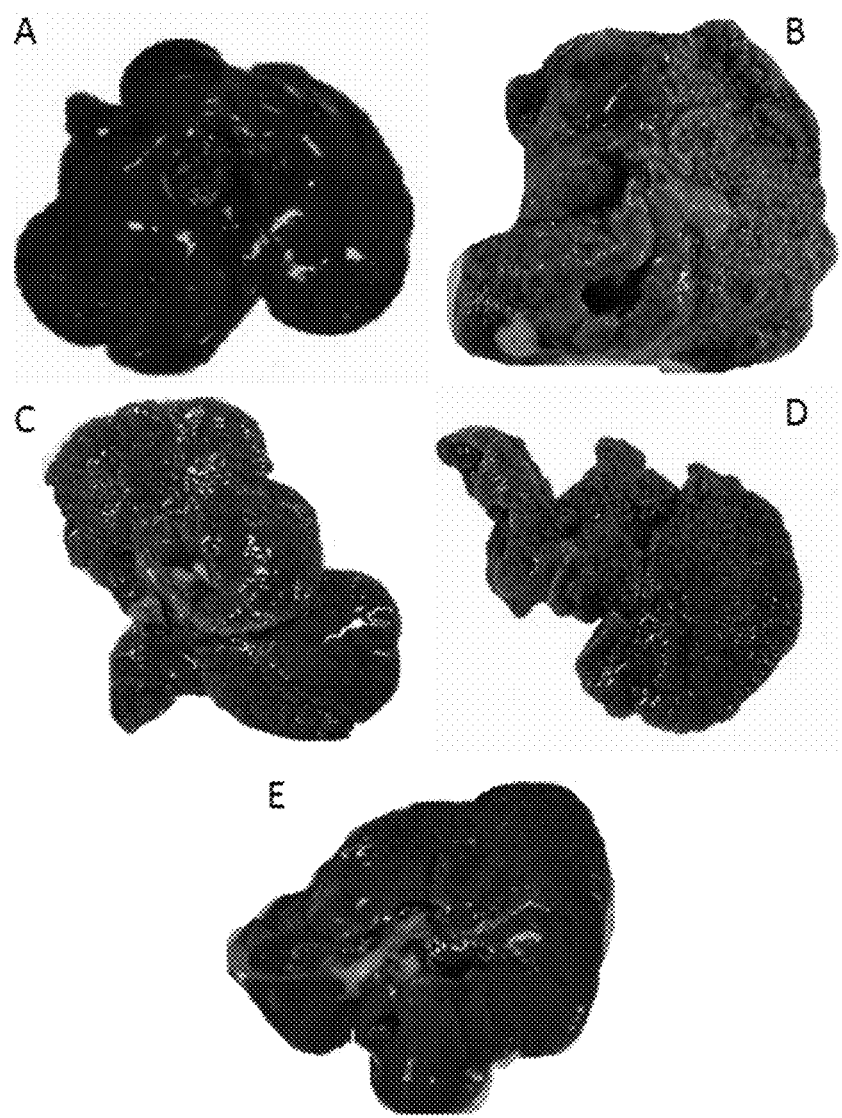
FIG. 3 is a comparison of the toxicity of different selenium products to rat liver.

After 3 months of administration, the liver lesions of rats in each experimental group are shown in FIG. 3, where A is a blank group, B is a sodium selenite group, C is a selenium-enriched yeast group, D is a selenoprotein group prepared in Comparative Example 3, and E is a *Cardamine violifolia* selenoprotein group prepared in Embodiment 1. It can be clearly seen that the sodium selenite group caused liver lesions, the selenium-enriched yeast group and the selenoprotein group prepared in Comparative Example 3 also had lesions to varying degrees, the *Cardamine violifolia* selenoprotein group prepared by the present disclosure was consistent with the blank control group, and no toxic effects were observed in the liver, proving that the *Cardamine violifolia* selenoprotein prepared by the present disclosure was non-toxic at the above doses.

The selenoprotein sample prepared in Comparative Example 3 also caused a certain degree of pathological changes. The reason was related to the preparation method, which resulted in the selenoprotein sample containing certain heavy metals and excessively high ash content, thereby damaging the liver.

The selenium in selenium-enriched yeast is mainly in the form of selenomethionine, which causes liver lesions of varying degrees. However, about 80% of the selenium in the selenoprotein prepared by the present disclosure is in the form of selenocysteine/selenocystine, which has no toxic effect on the liver. This further proves that the safety of Cardamine violifolia selenoprotein with selenocysteine/selenocystine as the characteristic components is higher than that of selenium-enriched yeast with selenomethionine as the main component and is much higher than inorganic selenium (sodium selenite).

Feeding rats with different doses of Cardamine violifolia selenoprotein standard samples (prepared in Embodiment 1), the doses calculated by selenium content were 0.15, 0.30, and 0.60 mgSe/kg, respectively. The total number and motility of sperm in each dose group are shown in the following table:

| dose mg/kgBW | total ×106/g | movement % | rapid movement % |
|---|---|---|---|
| 0 | 320.7 ± 130.3 | 85.4 ± 4.5 | 54.7 ± 9.7 |
| 187 | 296.2 ± 104.5 | 73.7 ± 24.7 | 48.1 ± 17.8 |
| 375 | 303.4 ± 98.4 | 82.0 ± 5.8 | 54.5 ± 6.2 |
| 749 | 293.0 ± 175.2 | 78.1 ± 17.4 | 54.1 ± 14.6 |
|  | $P > 0.05$ | $P > 0.05$ | $P > 0.05$ |

As can be seen from the above table, at each dosage, there was no significant change in the total number and motility of sperm, which proves that the Cardamine violifolia selenoprotein prepared by the present disclosure has high safety.

In summary, the technical indicators of the Cardamine violifolia selenoprotein standard sample prepared by the present disclosure can fully meet or even significantly exceed the national standard requirements for selenoproteins; it can also significantly increase the biological activity of glutathione peroxidase (GPX) in plasma, thereby improving antioxidant capacity; and it has good safety, so it is expected to fill the gap in selenoprotein standards on the market.

The above description is a preferred embodiment of the present disclosure, which cannot be used to limit the scope of rights of the present disclosure. For ordinary technicians in this technical field, any modifications, equivalent substitutions and improvements made within the spirit and principles of the present disclosure should be included in the protection scope of the present disclosure.

What is claimed is:

1. A preparation method to obtain highly safe and active selenoprotein from Cardamine violifolia, the preparation method comprising the following steps:
   step 1, hydrolyzing Cardamine violifolia powder with cellulase, performing cellulase deactivation treatment after the hydrolyzing, and then centrifuging to obtain a supernatant;
   step 2, adding an enzyme mixture comprising alkaline protease, trypsin, papain, protease K and protease XIV into the supernatant to perform enzymolysis and simultaneously performing electrodialysis on the supernatant mixture to remove heavy metal ions, inorganic selenium salt ions and then performing enzyme deactivation to obtain a reaction solution;
   step 3, concentrating and drying the reaction solution obtained in step 2 to obtain the selenoprotein in Cardamine violifolia.

2. The preparation method of claim 1, wherein the ratio of cellulose to total Cardamine violifolia used is 0.1~10% wt %, the hydrolysis temperature is 30~50° C. and hydrolysis time is 1~4 h.

3. The preparation method of claim 1, wherein the centrifugation is performed at 1000~10000 r/min for 5~60 minutes.

4. The preparation method of claim 1, wherein the ratio of enzyme mixture to total Cardamine violifolia used is 0.1~10% wt % and the enzymolysis temperature is 30~50° C.

5. The preparation method of claim 1, wherein the electrodialysis time is 0.5~8 h.

6. The preparation method of claim 1, wherein temperature of the cellulase deactivation treatment and the enzyme deactivation are both 85~95° C.

7. The preparation method of claim 1, wherein the drying, in step 3, is spray drying or freeze drying.

* * * * *